United States Patent [19]

Watanabe et al.

[11] 4,304,925

[45] Dec. 8, 1981

[54] PROCESS FOR PURIFYING ESTERS

[75] Inventors: Tsutomu Watanabe, Ikeda; Tadayoshi Kawakami, Izumi, both of Japan

[73] Assignee: Sekisui Kagaku Kogyo Kabushiki Kaisha, Osaka, Japan

[21] Appl. No.: 134,137

[22] Filed: Mar. 26, 1980

[30] Foreign Application Priority Data

Mar. 29, 1979 [JP] Japan .................................. 54-37358

[51] Int. Cl.$^3$ ........................... C09F 5/08; C11C 3/02
[52] U.S. Cl. ......................................... 560/78; 560/79; 560/103; 560/112; 560/191; 560/218; 560/248; 260/410.6; 260/410.9 R; 260/425
[58] Field of Search ..................... 260/410.9 R, 410.6, 260/425, 426; 560/78, 79, 103, 112, 191, 218, 248

[56] References Cited

FOREIGN PATENT DOCUMENTS

| 2604751 | 8/1977 | Fed. Rep. of Germany ........ 560/78 |
| 46-3718 | 11/1971 | Japan . |
| 49-54323 | 5/1974 | Japan . |
| 50-17043 | 6/1975 | Japan . |

Primary Examiner—John F. Niebling
Attorney, Agent, or Firm—Wenderoth, Lind & Ponack

[57] ABSTRACT

In a process for purifying an ester with little contamination by catalytic metal components in a high yield which comprises treating an esterification reaction mixture with a basic substance, said esterification reaction mixture being obtained by reacting an organic carboxylic acid or its anhydride with an alcohol in the presence of an organometallic compound as an esterification catalyst, and purifying the product in a manner known per se; the improvement wherein prior to said treatment with the basic substance, water is added to the esterification reaction mixture and the mixture is heated.

13 Claims, No Drawings

PROCESS FOR PURIFYING ESTERS

This invention relates to a process for purifying esters. More specifically, it relates to an improved process for recovering an ester with little contamination by catalytic metal components in a high yield from an esterification reaction mixture obtained by reacting an organic carboxylic acid or its anhydride with an alcohol in the presence of an organometallic compound as an esterification catalyst.

It has been known in the past that organometallic compounds, for example organotitanium compounds such as tetraisopropyl titanate, tetra-n-butyl titanate, tetra-2-ethylhexyl titanate or the polymers thereof, and organotin compounds such as tin oxalate, butyltin maleate or tin tetraethylate, are useful as catalysts in the production of esters by the reaction of organic carboxylic acids or the anhydrides thereof with alcohols. These catalysts have been widely used commercially.

In order to obtain a purified ester from an esterification reaction mixture obtained by using these esterification catalysts comprising organometallic compounds, it has been the general practice to add an aqueous alkaline solution to the esterification reaction mixture to simultaneously neutralize the unreacted or partially esterified organic carboxylic acid and hydrolyze the catalyst, remove the aqueous layer, wash the residue, subject the product to steam stripping or vacuum distillation, and further treat the product with activated carbon, activated clay, etc.

According to the aforesaid conventional method, which involves adding an aqueous alkaline solution to the esterification reaction mixture as obtained after the reaction and simultaneously neutralizing the unreacted or partially esterified organic carboxylic acid and hydrolyzing the catalyst, the organometallic compound catalyst is difficult to hydrolyze completely, and even when the crude ester is then treated with activated carbon or activated clay, the catalyst cannot completely be removed. Thus, the catalyst remains in the final ester product, and deteriorates the quality of the ester, especially its electrical insulation resistance.

Furthermore, the hydrolysis product of the esterification reaction product in such a purifying method is generally a viscous gel which is difficult to separate by filtration, and it is extremely difficult to perform an operation of separating the crude ester from the aqueous layer. This brings about the disadvantage that a large amount of the crude ester is entrained in the aqueous layer at the time of separating the aqueous layer from the organic layer in the neutralization and washing steps, and a large amount of the desired ester is lost.

Attempts have therefore been made to overcome such a disadvantage. For example, Japanese Laid-Open Patent Publication No. 3718/71 discloses a method which comprises contacting the esterification reaction mixture simultaneously with steam and a finely pulverized solid alkali at a temperature of more than 100° C. Japanese Patent Publication No. 54323/74 suggests a method which comprises heating the esterification reaction mixture together with an aqueous solution of an inorganic alkali at a temperature of 100° C. or more. Japanese Patent Publication No. 17043/75 discloses a method which comprises performing esterification in the presence of an alkaline substance, neutralizing the esterification reaction mixture with an alkaline substance as it is formed, removing the free alcohol by steam distillation, cooling the product, adding water, stirring the mixture vigorously at a temperature below the boiling point of water for at least 15 minutes, and removing the added water by vacuum distillation.

These methods, however, have their own disadvantages. For example, the first two methods involve removal of the hydrolysis product together with unreacted alkali or alkali metal salt, and therefore, it is difficult to separate it by filtration from the esterification reaction mixture. Further, this requires a large filtration area, and a long period of time is required for the filtration operation. Moreover, in the last-mentioned method, the hydrolysis of the catalyst is insufficient, and the purified ester has a high acid value. Furthermore, since the amount of metal contained is large, the electrical insulation resistance of the product is low.

According to the present invention, an improved process is provided which removes the defects of the conventional methods for purifying esters.

The present invention provides, in a process for obtaining an ester with little contamination by catalytic metal components in a high yield, which comprises treating an esterification reaction mixture with a basic substance, said esterification reaction mixture being obtained by reacting an organic carboxylic acid or its anhydride with an alcohol in the presence of an organometallic compound as an esterification catalyst, and purifying the product in a manner known per se, the improvement wherein prior to said treatment with the basic substance, water is added to the esterification reaction mixture and the mixture is heated.

The esterification reaction between an organic carboxylic acid or its anhydride and an alcohol in accordance with this invention can be carried out by a method known per se using an esterification catalyst comprising an organometallic compound.

Any organometallic compounds known heretofore to have a catalytic action in the esterification reaction between an organic carboxylic acid or its anhydride and an alcohol may be used as the organometallic compound catalyst in the above esterification reaction. Typical examples of the catalyst are shown below. It should be understood however that the invention is in no way limited by the following exemplification.

(I) Organotitanium compounds (I-1) Tetra ($C_3$–$C_{10}$) alkyl titanates such as tetra-n-butyl titanate, tetraisopropyl titanate, or tetra-2-ethylhexyl titanate.

(I-2) Organotitanium compounds of the formula $TiCl_n(OR)_{4-n}$ in which R represents a $C_1$–$C_{10}$ alkyl, aryl or aralkyl group, and n is an integer of 0 to 4, such as titanium tetrachloride, titanium chloride trimethoxide, titanium dichloride dibutoxide, titanium trichloride butoxide, titanium trichloride isopropoxide, titanium dichloride diethoxide, titanium tetraisopropoxide, and titanium tetrabutoxide.

(II) Organotin compounds (II-1) Tin tetra($C_1$–$C_6$) alkanolates such as tin tetramethylate, tin tetraethylate, tin tetrapropylate and tin tetraisobutylate.

(II-2) Organotin complexes such as butyltin maleate and dibutyltin dilaurate.

(II-3) Tin salts of organic acids such as tin oxalate.

The process of this invention brings about especially good results when the organotitanium compounds and organotin compounds, particularly organotitanium compounds having 3 to 8 carbon atoms such as tetra-n-butyl titanate, tetraisopropyl titanate and tetra-2-ethylhexyl titanate, and tin tetraethylate are used as the esterification catalyst.

A wide range of organic carboxylic acids, ranging from mono- to poly-basic acids, or from aliphatic to aromatic acids can be esterified using the aforesaid catalyst. Typical examples of the organic carboxylic acids are given below.

(a) Aliphatic monocarboxylic acids, for example saturated aliphatic monocarboxylic acids having up to 20 carbon atoms, such as myristic acid, palmitic acid or stearic acid; and unsaturated aliphatic monocarboxylic acids having up to 20 carbon atoms, such as oleic acid, linoleic acid and linolenic acid.

(b) Aliphatic polycarboxylic acids, for example saturated aliphatic dicarboxylic acids having up to 20, especially up to 10, carbon atoms such as adipic acid, sebacic acid, azelaic acid or hexahydrophthalic acid; saturated aliphatic tricarboxylic acids such as citric acid; and unsaturated aliphatic dicarboxylic acids such as fumaric acid and maleic acid.

(c) Aromatic monocarboxylic acids such as benzoic acid.

(d) Aromatic polycarboxylic acids such as phthalic acid, isophthalic acid, terephthalic acid, trimellitic acid, hemimellitic acid, and trimesic acid.

Of these, the aromatic polycarboxylic acids, saturated aliphatic dicarboxylic acids, and the anhydrides of these are preferred. Above all, phthalic acid, trimellitic acid, the anhydrides of these, and adipic acid are used advantageously.

On the other hand, alcohols which are used to esterify these organic acids may be exemplified as follows:

(a) Aliphatic monohydric alcohols, preferably having up to 20 carbon atoms, especially 1 to 3 carbon atoms, such as methyl alcohol, ethyl alcohol, isopropyl alcohol, n-butyl alcohol, isobutyl alcohol, sec-butyl alcohol, heptyl alcohol, n-octyl alcohol, 2-ethylhexyl alcohol, iso-octanol, iso-nonanol, iso-decanol, and tridecanol.

(b) Aliphatic dihydric alcohols, preferably having up to 10 carbon atoms, especially 2 to 8 carbon atoms, such as ethylene glycol, diethylene glycol, triethylene glycol, propylene glycol, dipropylene glycol, butylene glycol, and 2,2,4-trimethylpentanediol.

(c) Aliphatic polyhydric alcohols such as glycerol, and pentaerythritol.

These alcohols may be used as mixtures with each other, and aliphatic saturated monohydric alcohols having 1 to 13 carbon atoms are particularly preferred.

The reaction of the organic carboxylic acid or its anhydride with the alcohol in the presence of an esterification catalyst comprising the organometallic compound in this invention is carried out in a customary manner. Generally, the organic carboxylic acid or its anhydride is reacted with a slight excess of the alcohol in the presence of the esterification reaction catalyst comprising the organometallic compound in the absence of a solvent at a temperature of, usually, 100°-230° C.

The present invention pertains to a process for aftertreatment of the esterification reaction mixture formed as a result of such an esterification reaction. While in the prior art, the esterification reaction mixture as formed is directly treated with an alkali, the process of this invention is characteristic in that water is first added to the esterification reaction mixture after the reaction and then the mixture is heat-treated, before it is submitted to treatment with a basic substance.

The aforesaid esterification reaction mixture to be treated by the process of this invention has an acid value of generally not more than 1.0 for example 0.05–1.0, preferably 0.05–0.5, in mg KOH/g.

The amount of water to be added to the esterification reaction mixture is not strictly limited, but generally, the amount of water may be at least 5% by weight, preferably 5 to 50% by weight, more preferably 5 to 20% by weight, based on the weight of said esterification reaction mixture.

The heating temperature for the esterification reaction mixture to which water has been added is not critical, but generally it is advantageous that heating is carried out at a temperature of about 50° C. to 100° C., the reflux temperature, preferably 60° to 98° C., more preferably 80° to 98° C.

Heating is carried out until the catalyst present in the esterification reaction mixture is substantially completely hydrolyzed. The time so required is usually at least 30 minutes, and preferably about 1 to about 2 hours.

By the heat-treatment after the addition of water, the organometallic compound catalyst present in the esterification reaction mixture is hydrolyzed and dispersed finely as a fine powder.

The esterification reaction mixture which has thus been heat-treated in the presence of water is then treated with a basic substance. Suitable basic substances are the hydroxides, carbonates or bicarbonates of alkali metals. Examples are sodium hydroxide, potassium hydroxide, sodium carbonate, potassium carbonate, sodium bicarbonate and potassium bicarbonate. Sodium carbonate is preferred.

These basic substances may be added in the form of a solid powder or aqueous solution to the esterification reaction mixture. The amount of the basic substance should be sufficient at least to neutralize the esterification reaction mixture. The residual acidity of the esterification reaction mixture can be easily measured. The theoretical amount of a base required to neutralize the residual acidity can be obtained by calculation. In the present invention, the desirable amount of the basic substance is about 5 to about 10 equivalent times the stoichiometrical amount.

The treatment with the basic substance may be generally carried out at room temperature to about 98° C. by stirring the esterification reaction mixture to which the basic substance has been added.

By the treatment with the basic substance, the catalyst components are hydrolyzed and settle to the bottom of the aqueous layer with ease as a precipitate at the time of separating the esterification reaction mixture from the aqueous layer, and the residual acidic substance in the esterification reaction mixture changes to a water-soluble salt and migrates into the aqueous layer. Thus, according to the process of this invention, the catalyst components and the residual acidic substance can be easily removed from the esterification reaction mixture by a very simple operation of separating the aqueous layer.

The reaction mixture obtained by removing the settled catalyst components and separating the aqueous layer can be further purified as required. This purification can be performed in accordance with a method known per se. For example, it can be purified by adding water, washing it with water and subsequently separating the aqueous layer. Moreover, by removing the unreacted alcohol by distillation under reduced pressure or at elevated temperatures, or by performing treatment with activated clay, activated carbon, diatomaceous earth, etc., an ester of high purity can be obtained in a good yield.

Since the process of this invention is characterized by adding water to the esterification reaction mixture after the esterification reaction, heating the mixture to hydrolyze the organometallic compound catalyst contained in the esterification mixture and then neutralizing the residual acidic substance by addition of an alkali, the hydrolysis of the catalyst can be completely carried out. This is a significant advantage over the prior technique involving adding an aqueous alkaline solution to the as-obtained esterification reaction mixture to simultaneously hydrolyze the catalyst and neutralize the unreacted organic acid. Moreover, the process of this invention has a very significant technical advance in that the product of hydrolysis is a non-tacky settleable precipitate which can be easily separated.

According to the process of this invention, therefore, the separation of the aqueous layer, the washing of the product with water, etc., which are to be performed subsequent to the treatment with basic substances, can be carried out with very good operability and simplicity within very short periods of time. In addition, the amount of the ester which is lost by migration into the aqueous layer can be minimized. Hence, the process of this invention is advantageous in operability and economy.

Furthermore, according to the process of this invention, the amount of metal as a catalyst residue in the final ester product can be greatly reduced, and therefore, the quality of the ester can be increased. For example, according to this invention, the volume inherent resistivity of the ester, which is important in its application as a plasticizer, can be increased to a greater degree than in the prior art.

The esters purified by the process of this invention have superior electrical insulating property, heat stability, water resistance, resistance to bleeding, etc., and can be advantageously used as plasticizers for processing vinyl-type synthetic resins into vinyl-coated cables and wires, artificial leathers, and films.

The following examples illustrate the process of this invention.

The "volume inherent resistivity" in these examples was measured by JIS K-6751 (Method for Testing Phthalic Esters); the "metal content" of the purified ester, by atomic absorptiometry; and the "ester content" of the aqueous layer, by JIS K-0102 (Method A for n-Hexane-Extractable Substances).

EXAMPLE 1

Phthalic anhydride (6.0 kg) and 12.12 kg of 2-ethylhexyl alcohol were introduced into a reactor equipped with a reflux condenser and a water separator, and with stirring. They were heated to form a solution. Then, 30 g of tetra-n-butyl titanate was added to the solution as a catalyst. The mixture was heated at 200° C. for 45 hours under reduced pressure to afford an esterification reaction mixture (acid value 0.22 mg KOH/g) having a degree of esterification of 99.83%.

The esterification reaction mixture was cooled. 1.0 Kg of the reaction mixture was taken, and 150 g (15% by weight based on the weight of the esterification reaction mixture) of water was added. The mixture was heated at 95° C. for 120 minutes with stirring to hydrolze the tetra-n-butyl titanate. Then, 1.7 g of powdery sodium carbonate was added to neutralize the mono-2-ethylhexyl phthalate for 30 minutes. Then, the crude ester was separated from the aqueous layer. After the addition of sodium carbonate, the hydrolyzate precipitated to the bottom of the aqueous layer, and the separation of the crude ester from the aqueous layer was completed in 10 minutes. Then, 400 g (40% by weight based on the crude ester) of water was added to the crude ester to wash it. The aqueous layer was separated in 5 minutes. Steam was blown under reduced pressure into the crude ester after separation to remove the excess of 2-ethylhexyl alcohol completely. Furthermore, the residue was treated with activated clay, and filtered to form a purified ester. The amount of the catalytic metal contained in the purified ester and its volume inherent resistivity and acid value were measured. The amount of the ester contained in the aqueous layer separated from the crude ester was measured. The results are shown in Table 1 in the column of Run No. 1.

Using the remainder of the esterification reaction mixture (1 Kg) obtained by the aforesaid esterification reaction, the operation of purifying the ester was performed in the same way as above except that the hydrolyzing conditions and/or neutralizing conditions were changed as shown in Runs Nos. 2 to 6 in Table 1. The catalytic metal content, volume inherent resistivity, acid value and ester content in the aqueous layer of each of the purified esters were measured, and the results are also shown in Table 1.

Comparative Example 1

For comparison, 150 g of a 5% aqueous solution of sodium carbonate was added to 1.0 kg of the same esterification reaction mixture as obtained in Example 1, and the mixture was stirred at 95° C. to perform the neutralization of the unreacted mono-2-ethylhexyl phthalate and hydrolysis of tetra-n-butyl titanate for 120 minutes. A viscous gel-like product was formed. Then, an operation of separating the crude ester from the aqueous layer was performed. This operation required a period of more than one hour because the viscous gel-like product existed on the interface between the crude ester and the aqueous layer. The crude ester so separated was subjected to the same operation as in Example 1, and the resulting product was tested in the same way as in Example 1. The results are shown in Table 1.

Comparative Example 2

Phthalic anhydride (250 g) and 505 g of 2-ethylhexyl alcohol were introduced into a reactor equipped with a reflux condenser and a water separator, and 0.15 cc of tetraisopropyl titanate as a catalyst was added. The mixture was stirred, and 0.4 cc of a 10% by weight aqueous solution of sodium hydroxide was added. The reaction was performed at 220° C. under reduced pressure. In 4.5 hours, an esterification reaction mixture having an acid value of mg KOH/g was obtained. After the reaction, the excess of the alcohol was distilled off under reduced pressure, and by blowing steam at 180° C. under reduced pressure to distill off the alcohol completely. The residue was treated with activated clay, and then the precipitate of the titanium catalyst together with sodium hydroxide were separated at a pressure of 50 mmHg.ab. using a filter (78.5 cm$^2$) to obtain a purified ester. The time required for filtration was 2 hours and 10 minutes. The catalyst metal content, volume inherent resistivity and acid value of the purified ester were measured, and the results are shown in Table 1.

Comparative Example 3

Phthalic anhydride (250 g) and 659 g of 2-ethyl hexyl alcohol were introduced into a reactor equipped with a reflux condenser and a water separator, and with stirring, they were heated to form a solution. Then, 0.375 g of tetra-n-butyl titanate as a catalyst was added, and the reaction was performed at 210° C. and 200 to 160 mmHg ab. for 4.5 hours to form an esterification reaction mixture having a degree of esterification of 99.85% (acid value 0.16 mg KOH/g).

Then, the pressure was gradually reduced to 5 mmHg ab. to distill off the excess of the alcohol. At this time, the temperature decreased to 184° C. With stirring, 3.7 g of a 25% aqueous solution of sodium hydroxide was added to the resulting esterification reaction mixture. The acid value of the esterification reaction mixture became 0.03 mg KOH/g. Subsequently, the mixture was subjected to steam distillation at 180° to 185° C. and 30 mmHg ab. until no distillation of residual alcohol was detected. The residue was cooled to 95° C., and 10 ml of water was added. The mixture was stirred at 350 rpm for 30 minutes, and dehydrated at 1 mmHg ab. and 95° C. to obtain an ester having a water content of 0.022%. The ester was filtered under a pressure of 50 mmHg ab. by a filter (78.5 cm$^2$) to separate a precipitate of the titanium catalyst together with sodium hydroxide. The time required for filtration was 25 minutes.

The acid value, catalytic metal content and volume inherent resistivity of the resulting purified ester were measured, and the results are shown in Table 1.

Comparative Example 4

Phthalic anhydride (250 g) and 505 g of 2-ethylhexyl alcohol were introduced into a reactor equipped with a reflux condenser and a water separator, and the mixture was heated to form a solution. Then, 0.375 g of tetra-n-butyl titanate as a catalyst was added, and the reaction was performed at 200 to 160 ab. mmHg and 210° C. for 4.5 hours to form an esterification reaction mixture having a degree of esterification of 99.83% and an acid value of 0.18 mg KOH/g. Then, the pressure was gradually reduced down to 5 mmHg ab., and while distilling off the excess of alcohol, the mixture was allowed to cool. When the temperature reached 150° C., nitrogen gas was introduced to return the pressure to normal atmospheric pressure. Powdery sodium carbonate (1.2 g) was added, and while blowing steam at 150° C. and 20 mmHg ab., steam distillation was carried out until no more alcohol distilled. The residue was dehydrated at 150° C. and 5 mmHg ab. for 30 minutes, and cooled to 95° C. The sodium carbonate and the precipitate of the titanium catalyst were separated by filtration under a pressure of 50 mmHg ab. by a filter (78.5 cm$^2$). The time required for filtration was 43 minutes.

The acid value, catalytic metal content and volume inherent resistivity of the resulting purified ester were measured, and the results are shown in Table 1.

TABLE 1

| Run | | Example 1 | | | | | | Comparative Example | | | |
|---|---|---|---|---|---|---|---|---|---|---|---|
| | | No. 1 | No. 2 | No. 3 | No. 4 | No. 5 | No. 6 | 1 | 2 | 3 | 4 |
| Hydrolyzing conditions | Amount of water % | 15 | 10 | 15 | 50 | 5 | 5 | — | — | — | — |
| | Temperature (°C.) | 95 | 95 | 95 | 80 | 60 | 60 | — | — | — | — |
| | Time (minutes) | 120 | 60 | 30 | 90 | 120 | 30 | — | — | — | — |
| Neutralizing conditions | Alkali | Na$_2$CO$_3$ | Na$_2$CO$_3$ | Na$_2$CO$_3$ | Na$_2$CO$_3$ | Na$_2$CO$_3$ | NaOH | Na$_2$CO$_3$ | — | NaOH | Na$_2$CO$_3$ |
| | Amount of alkali (g) | 1.7 (powder) | 1.7 (powder) | 1.7 (powder) | 1.7 (powder) | 85 as 2% aq. sol. | 1.2 (solid) | 150 as 5% aq.sol. | — | 3.7 as 25% aq.sol. | 1.2 (powder) |
| | Time (minutes) | 30 | 30 | 30 | 30 | 30 | 30 | 120 (95° C.) | — | — | — |
| Ester content in the aqueous layer (g/kg of the esterification mixture) | | 0.013 | 0.020 | 0.032 | 0.035 | 0.042 | 0.103 | 0.520 | — | — | — |
| Content of catalytic metal (titanium) (ppm) | | 0.08 | 0.13 | 0.15 | 0.12 | 0.83 | 0.75 | 5.73 | 8.35 | 2.81 | 7.25 |
| Volume inherent resistivity (ohm-cm at 30° C.) | | 3.85 × 10$^{12}$ | 3.32 × 10$^{12}$ | 2.85 × 10$^{12}$ | 3.16 × 10$^{12}$ | 2.43 × 10$^{12}$ | 1.96 × 10$^{12}$ | 8.03 × 10$^{11}$ | 7.48 × 10$^{11}$ | 9.45 × 10$^{11}$ | 8.11 × 10$^{11}$ |
| Acid value (mg KOH/g) | | 0.005 | 0.002 | 0.002 | 0.003 | 0.003 | 0.005 | 0.009 | 0.036 | 0.032 | 0.042 |

EXAMPLE 2

An esterification reaction mixture (acid value 0.41 mg KOH/g) was prepared in the same way as in Example 1 except that 5.9 kg of adipic acid was used instead of 6.0 kg of phthalic anhydride. One-kilogram portions taken from the resulting esterification reaction mixture were each subjected to the hydrolysis and neutralization conditions shown in Runs Nos. 1 to 3 in Table 2 to obtain purified esters. Each of the esters obtained was tested in the same way as in Example 1, and the results are shown in Table 2.

Comparative Example 5

To 1.0 kg of the esterification reaction mixture obtained in Example 2 was added 50 g of a 10% by weight aqueous solution of sodium hydroxide, and the mixture was stirred at 95° C. to neutralize the esterification reaction mixture and hydrolyze the catalyst for 90 minutes. Then, an operation of separating the esterification reaction mixture from the aqueous layer was performed. More than 1 hour was required to performed the separating operation because of the presence of a viscous gel-like material. The crude ester after the separation was subjected to the same purifying operation as in Example 1. The purified ester was tested in the same way as in Example 1, and the results are shown in Table 2.

Comparative Example 6

Comparative Example 2 was repeated except that 246 g of adipic acid was used instead of 250 g of phthalic anhydride. The results are shown in Table 2.

Comparative Example 7

One kilogram of the esterification reaction mixture prepared in Example 2 was taken, and treated in the same way as in Comparative Example 3. The time required for separating the precipitate of the titanium catalyst and sodium hydroxide by filtration was 27 minutes. The acid value, catalytic metal content and volume inherent resistivity of the product were measured. The results are shown in Table 2.

Comparative Example 8

One kilogram of the esterification reaction mixture prepared in Example 2 was taken, and treated in the same way as in Comparative Example 4. The time required for filtration to separate the precipitate of the titanium catalyst and sodium carbonate was 46 minutes. The acid value, catalytic metal content and volume inherent resistivity of the resulting product were measured. The results are shown in Table 2.

Comparative Example 9

The same esterification reaction mixture as prepared in Example 3 was subjected to the same operation as in Comparative Example 1. The results are shown in Table 3.

Comparative Example 10

One kilogram of the esterification reaction mixture prepared in Example 3 was taken, and subjected to the same operation as in Comparative Example 3. The time required to separate the precipitate of the tin catalyst and sodium hydroxide by filtration was 29 minutes. The acid value, catalytic metal content and volume inherent resistivity of the purified ester were measured, and the results are shown in Table 3.

EXAMPLE 4

An esterification reaction mixture (acid value 0.32 mg KOH/g) was prepared in the same way as in Example 1 except that 10.8 kg of heptyl alcohol was used instead of 12.12 kg of 2-ethylhexyl alcohol, and 30 g of tetraisopropyl titanate was used instead of 30 g of tetra-n-butyl titanate. One kilogram of the resulting esterification reaction mixture was taken, and treated under the conditions shown in Table 3. The results are shown in Table 3.

TABLE 2

| Run | | Example 2 | | | Comparative Example | | | |
|---|---|---|---|---|---|---|---|---|
| | | No. 1 | No. 2 | No. 3 | 5 | 6 | 7 | 8 |
| Hydrolyzing conditions | Amount of water added (%) | 5 | 15 | 10 | — | — | — | — |
| | Temperature (°C.) | 80 | 95 | 60 | — | — | — | — |
| | Time (minutes) | 60 | 60 | 60 | — | — | — | — |
| Neutralizing conditions | Alkali | NaOH | NaOH | NaOH | NaOH | — | NaOH | $Na_2CO_3$ |
| | Amount of the alkali (g) | 1.2 (solid) | 1.2 (solid) | 1.2 (solid) | 50 as 10% aq. sol. | — | 3.7 as 25% aq. sol. | 1.2 (solid) |
| | Time (minutes) | 30 | 30 | 30 | 90 at 95° C. | — | — | — |
| Ester content in the aqueous layer (g/kg of the esterification mixture) | | 0.04 | 0.10 | 0.05 | 0.73 | — | — | — |
| Catalytic metal content as titanium (ppm) | | 0.12 | 0.09 | 0.11 | 7.48 | 10.52 | 3.12 | 6.73 |
| Volume inherent resistivity (ohms.cm at 30° C.) | | $2.35 \times 10^{12}$ | $2.56 \times 10^{12}$ | $2.08 \times 10^{12}$ | $7.32 \times 10^{11}$ | $9.18 \times 10^{11}$ | $9.65 \times 10^{11}$ | $8.46 \times 10^{11}$ |
| Acid value (mg KOH/g) | | 0.003 | 0.002 | 0.003 | 0.008 | 0.029 | 0.030 | 0.03 |

EXAMPLE 3

An esterification reaction mixture (acid value 0.15 mg KOH/g) was prepared in the same way as in Example 1 except that 14.7 kg of isodecyl alcohol was used instead of 12.12 kg of 2-ethylhexyl alcohol, and tin tetraethylate was used instead of tetra-n-butyl titanate. One-kilogram portions taken from the resulting esterification reaction product were each subjected to hydrolysis and neutralization under the conditions shown in Runs Nos. 1 to 3 in Table 3, and further purified in the same way as in Example 1 to form purified esters. The results are shown in Table 3.

Comparative Example 11

The esterification reaction mixture prepared in Example 4 was treated in the same way as in Comparative Example 1. The results are shown in Table 3.

Comparative Example 12

One kilogram of the esterification reaction mixture prepared in Example 3 was treated in the same way as in Comparative Example 4. The time required to separate the precipitate of the tin catalyst and sodium carbonate by filtration was 43 minutes. The acid value, catalytic metal content and volume inherent resistivity of the resulting ester were measured, and the results are shown in Table 3.

TABLE 3

| Run | | Example 3 | | | Example 4 | Comparative Example | | | |
|---|---|---|---|---|---|---|---|---|---|
| | | No. 1 | No. 2 | No. 3 | | 9 | 10 | 11 | 12 |
| Hydrolyzing conditions | Amount of water (g) | 5 | 10 | 50 | 10 | — | — | — | — |
| | Temperature (°C.) | 95 | 75 | 85 | 85 | — | — | — | — |

TABLE 3-continued

| Run | | Example 3 No. 1 | No. 2 | No. 3 | Example 4 | Comparative Example 9 | 10 | 11 | 12 |
|---|---|---|---|---|---|---|---|---|---|
| Neutralizing conditions | Time (minutes) | 60 | 60 | 120 | 60 | — | — | — | — |
| | Alkali | $Na_2CO_3$ | $Na_2CO_3$ | $Na_2CO_3$ | $Na_2CO_3$ | $Na_2CO_3$ | NaOH | $Na_2CO_3$ | $Na_2CO_3$ |
| | Amount of alkali (g) | 1.4 (powder) | 1.4 (powder) | 1.4 (powder) | 15 as 10% aq. sol. | 70 as 10% aq. sol. | 3.7 as 25% aq. sol. | 80 as 10% aq. sol. | 1.2 (powder) |
| | Time (minutes) | 30 | 30 | 30 | 30 | 90 at 95° C. | — | 60 at 85° C. | — |
| Ester content of the aqueous layer (g/kg of the esterfication mixture) | | 0.07 | 0.08 | 0.10 | 0.09 | 0.75 | — | 0.64 | — |
| Catalytic metal content (ppm) | | 0.45 (Ti) | 0.23 (Sn) | 0.15 (Sn) | 0.74 (Ti) | 4.52 (Sn) | 4.15 (Sn) | 3.46 (Ti) | 3.32 (Sn) |
| Volume inherent resistivity (ohms. cm at 30° C.) | | $3.42 \times 10^{12}$ | $3.95 \times 10^{12}$ | $4.16 \times 10^{12}$ | $6.75 \times 10^{11}$ | $9.32 \times 10^{11}$ | $1.04 \times 10^{12}$ | $2.16 \times 10^{11}$ | $9.48 \times 10^{12}$ |
| Acid value (KOH mg/g) | | 0.003 | 0.005 | 0.002 | 0.002 | 0.008 | 0.038 | 0.035 | 0.041 |

What we claim is:

1. In a process for recovering a purified ester from an esterification reaction mixture obtained by reacting an organic carboxylic acid or its anhydride with an alcohol in the presence of an organometallic compound as an esterification catalyst, which comprises adding a basic substance to said esterification reaction mixture, and purifying the ester, the improvement wherein, prior to said addition of said basic substance, water is added to said esterification reaction mixture and the resultant mixture is heated.

2. The process of claim 1 wherein the amount of water added to said esterification reaction mixture is 5 to 50% by weight based on the weight of said esterification reaction mixture.

3. The process of claim 2 wherein the amount of water added to said esterification reaction mixture is 5 to 20% by weight based on the weight of said esterification reaction mixture.

4. The process of claim 1 wherein said esterification reaction mixture to which water has been added is heated at a temperature of 60° to 98° C.

5. The process of claim 4 wherein said esterification reaction mixture to which water has been added is heated at a temperature of 80° to 98° C.

6. The process of claim 4 or 5 wherein said heating is carried out for at least 30 minutes.

7. The process of claim 1 wherein said esterification reaction mixture has an acid value of not more than 1.0 mg KOH/g.

8. The process of claim 1 wherein said esterification catalyst is an esterification catalyst comprising an organotitanium compound or an organotin compound.

9. The process of claim 1 wherein said basic substance is an alkali metal hydroxide, carbonate or bicarbonate.

10. The process of claim 1 wherein said organic carboxylic acid is phthalic acid, phthalic anhydride, trimellitic acid, trimellitic anhydride, or adipic acid.

11. The process of claim 1 wherein said organic carboxylic acid anhydride is phthalic anhydride.

12. The process of claim 1 wherein said alcohol is an aliphatic monohydric alcohol having 1 to 13 carbon atoms.

13. The process of claim 12 wherein said alcohol is 2-ethylhexyl alcohol.

* * * * *